United States Patent
Rana et al.

(10) Patent No.: US 8,364,501 B2
(45) Date of Patent: *Jan. 29, 2013

(54) ELECTRONIC APPOINTMENT SCHEDULING FOR MEDICAL RESOURCES

(75) Inventors: Sumit Rana, Madison, WI (US); Davin Sannes, Mount Horeb, WI (US); Matt Sidney, Madison, WI (US); Sashi Bellam, Madison, WI (US); Sapan Anand, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 287 days.

This patent is subject to a terminal disclaimer.

(21) Appl. No.: 12/748,928

(22) Filed: Mar. 29, 2010

(65) Prior Publication Data

US 2010/0185465 A1 Jul. 22, 2010

Related U.S. Application Data

(63) Continuation-in-part of application No. 10/914,471, filed on Aug. 9, 2004, now abandoned.

(51) Int. Cl.
G06Q 50/00 (2006.01)
(52) U.S. Cl. ............................................. 705/2; 705/3
(58) Field of Classification Search .................... 705/2, 3
See application file for complete search history.

(56) References Cited

U.S. PATENT DOCUMENTS

| 5,572,421 A | * | 11/1996 | Altman et al. ............ 705/3 |
| 6,389,454 B1 | * | 5/2002 | Ralston et al. ............ 709/204 |
| 2002/0040305 A1 | * | 4/2002 | Nakatsuchi et al. ............ 705/2 |
| 2003/0028402 A1 | * | 2/2003 | Ulrich et al. ............ 705/3 |
| 2004/0158486 A1 | * | 8/2004 | Nudd et al. ............ 705/8 |
| 2004/0243435 A1 | * | 12/2004 | Williams ............ 705/2 |

* cited by examiner

*Primary Examiner* — Gerald J. O'Connor
*Assistant Examiner* — Neha Patel
(74) *Attorney, Agent, or Firm* — Boyle Fredrickson, S.C.

(57) ABSTRACT

A computer-implemented system for scheduling patient appointments including a patient interface terminal configured to receive a patient identifier and to display a patient-specific listing of reasons for a medical appointment. The system further includes a computer system adapted for receiving the patient identifier, generating the patient-specific listing of reasons for a medical appointment based on an electronic medical record associated with the patient identifier and a comprehensive listing of reasons stored in a reasons database, receiving a selected reason for a requested medical appointment from the patient interface terminal, and generating and providing one or more specialized appointment scheduling options based on a combination of the selected reason and data from the electronic medical record associated with the patient identifier, the specialized appointment scheduling options including scheduling options for specialized medical resources specifically associated with the combination.

23 Claims, 5 Drawing Sheets

ELECTRONIC APPOINTMENT SCHEDULING FOR MEDICAL RESOURCES

CROSS REFERENCE TO RELATED APPLICATIONS

This application is a continuation in part of U.S. patent application Ser. No. 10/914,471, filed Aug. 9, 2004 now abandoned, and incorporated herein in its entirety.

BACKGROUND OF THE INVENTION

The present invention relates to electronic medical record (EMR) systems and in particular to an EMR system allowing access to and entry of data by a patient to request and schedule appointments and medical resources for the patient.

Scheduling of medical providers, equipment, laboratory services, and other resources for patient appointments is a significant challenge in efficiently controlling medical resources and costs. Typically, scheduling is controlled by employees in a clinic or other medical facility, who communicate with the patients by phone and arrange the schedules manually. While, in some cases, these employees can arrange all of the resources required for a visit, frequently patients are required to schedule multiple procedures in a series of tests through a series of phone calls to different employees handing scheduling for related, but separate, facilities. Such arrangements can be time consuming and inefficient, both for the patients and the medical facilities.

Enlisting patients as active participants in their own healthcare can increase patient satisfaction and the quality of the healthcare experience while decreasing the cost of providing that care. One area in which patient satisfaction can be dramatically improved, therefore, is in providing greater control and easier access for the patient to request and schedule appointments for medical care. Providing such control to the patient also affords benefits to the medical facilities, as when scheduling is done by the patient, there is a reduced need for scheduling personnel.

As it is desirable to allow patients access to scheduling of their procedures in order to improve efficiency, a number of medical communities have used the Internet to allow patients to directly schedule appointments. These systems, however, have not proved to be particularly efficient for a number of reasons. First, known scheduling systems typically provide scheduling capabilities only in predetermined increments of time. These systems, therefore, cannot tailor the amount of time necessary for an appointment to the reason for the appointment, and therefore are not efficient in scheduling the time of medical personnel and resources.

Furthermore, when patients schedule their own appointments, it is difficult for medical personnel to obtain necessary information from and provide necessary information to the patient prior to the visit. Therefore, for example, patients can arrive for appointments, and spend up to an hour filling out forms prior to meeting with a doctor. Additionally, as the medical practitioner does not know the reason for the visit prior to the arrival of the patient, the medical practitioner cannot prepare for the visit by providing instructions to the patient prior to the visit. This problem is particularly acute when evaluation of a medical problem requires multiple steps, such as, for example, laboratory work prior to meeting with a medical practitioner. Inadequate information, therefore, often results in return visits, which could have been easily avoided had sufficient information been available to both the patient and the physician.

SUMMARY OF THE INVENTION

The present invention provides a system for electronically scheduling medical resources. The system includes both a patient interface terminal, such as an internet terminal or a kiosk, and a computer system receiving time frame information and a reason for a medical appointment scheduling information from the patient interface terminal. Based on the information received, the computer system identifies a requested medical service, identifies resources required for the service, and presents schedule options at the interface terminal based on the identified medical services and resources. Because the reason for the visit is known, the computer system can schedule a time frame based on the reason for the appointment, thereby increasing efficiency. The resources scheduled can include a medical practitioner, and can also be a geographic office location, medical equipment, laboratory time, or other resource necessary for a selected healthcare service. After schedule options are provided to the patient, the computer system can accept an input from the patient interface terminal to select an appointment from the schedule options, and submit the appointment data to a schedule for the healthcare provider in real time to directly schedule an appointment. As described below, when scheduling an appointment, the system automatically provides targeted questionnaires and necessary information for the appointment to assure that both the patient and the healthcare provider have necessary information before the appointment. These steps increase efficiency in the healthcare system, also as described more fully below.

In another aspect of the invention, the scheduling system can receive a range of schedule times or a range of geographic locations acceptable for the appointment, and can present schedule options for resources available within the range of schedule times or geographic locations. The scheduling system can also communicate with a database providing data indicating appointment lengths for different types of healthcare service appointments, and present a schedule of options which accommodate an appointment of the required length. The schedule options presented can also be filtered to indicate only healthcare providers and resources that can be coordinated in both time and geography to provide the healthcare service.

In still another aspect of the invention, the scheduling system can provide a reminder or alert notification to the patient interface terminal. The alerts can be either provided at predetermined intervals or at a time selected by the patient through the patient interface terminal. The scheduling system can also receive from the patient interface terminal a notice of appointment cancellation and submit cancellation data to a schedule for the resource.

In still another aspect of the invention, the scheduling system can include a central database holding schedules for healthcare providers and resources, and can accesses the central database to identify healthcare providers for the service and identify resources required for the service to present schedule options according to common schedule openings of healthcare providers and resources. The common schedule openings can also be provided for healthcare providers and resources within a predetermined geographic range.

In yet another aspect of the invention, the schedule system of the present invention can accommodate the scheduling of healthcare services requiring multiple sequential steps. The computer system can identify healthcare providers and resources for each step of the service, and provide different combinations of the multiple providers and resources. Thus, for example, in a multi-step process, the first step can require a laboratory test and the computer system communicates with a database providing data indicating laboratory test processing delay, and the computer system can determine the steps appropriately to accommodate the required delay. The scheduling system can also communicate with a database providing travel time delays between the geographic locations and present schedule options which accommodate the travel time delay. The computer system can also store the series of steps together in a log or other data structure such that, if a cancellation request is received; all steps for the procedure are cancelled.

In yet another aspect of the invention, a system for scheduling patient appointments is provided which includes a patient interface terminal and a computer system scheduler communicatively coupled to the patient interface terminal and to a medical record database which includes medical data for specific patients. The computer system is adapted to receive data from the patient interface terminal to identify a patient making a request, and to filter medical services available to the patient based on the patient identity. By identifying the patient, it is possible to filter healthcare services, information, and data based on the age, sender, or history of the patient, to provide improved healthcare service.

In yet another aspect of the invention, the computer system can be further adapted to provide information to the patient based on a reason for the medical appointment, and receive data from the patient based on the reason for the medical appointment. In particular, the computer system can provide detailed questionnaires at the patient terminal which are tailored to obtain data for a particular medical appointment and/or medical resource. To increase efficiency, the computer system can also populate the questionnaire with available data from the medical records database and/or filter the questions provided to the patient based on known data about the patient.

In yet another aspect of the invention, the computer system can be adapted to provide access to specialized scheduling options where a combination of a patient selected reasons and data from the EMR indicate this option is available. This aspect allows a patient to get specific and more specialized care where indicated based on their selected reason and the EMR data.

These particular objects and advantages may apply to only some embodiments falling within the claims and thus do not define the scope of the invention.

DETAILED DESCRIPTION OF THE PREFERRED EMBODIMENT

Figure 1:
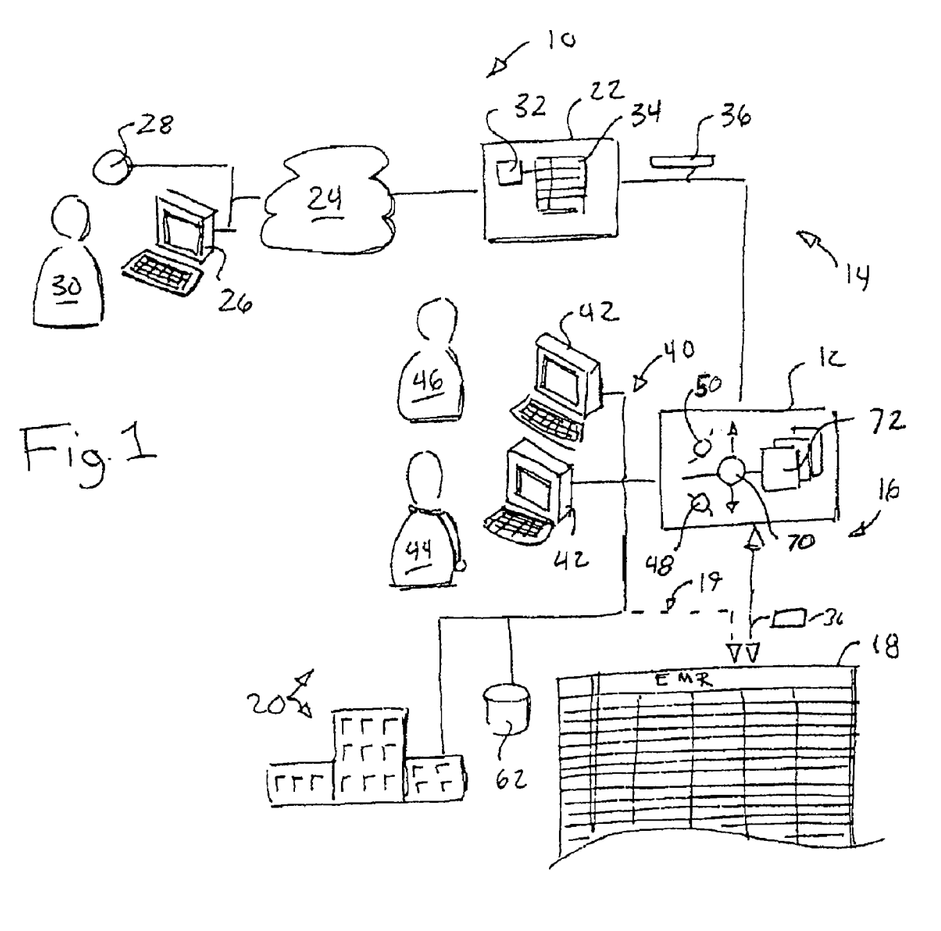
FIG. 1 is a simplified block diagram of a computerized interface for an EMR providing an Internet communication channel.

Referring now to FIG. 1, a patient scheduling system 10 per the present invention may include an interface module 12 standing between a patient communication channel 14 and an EMR communication channel 16, the latter communicating with an electronic medical record (EMR) database 18. Generally the interface module 12 is a program that may be physically located on an independent computer or run on a computer shared with another function such as the EMR database 18.

Generally, the EMR database 18 includes a complete medical history of many patients collected from a variety of healthcare sources 20 including physicians and other healthcare professionals such as members of the staff at hospitals, clinics, and laboratories communicating on standard EMR network 19. As will be understood to those of ordinary skill in the art, the EMR database 18 includes biographical information describing the patient, including the patient's age, gender, height and weight, and medical history information including the patient's medical conditions, previous medical procedures, medications, and laboratory test results. The EMR database 18 may be centrally accessed by many different healthcare sources 20 and thus serve as a path of intercommunication among many individuals working together to deliver healthcare.

The EMR database 18 is depicted as a single logical flat file for simplicity but may be configured in any of a variety of well known database formats including a relational database structure, an object database structure, and the like. The data of the EMR database 18, like all medical records, is protected under federal law to ensure that sensitive data of this record is not released in a way that would violate a patient's privacy rights. EMR databases may be obtained from a variety of commercial sources including Epic Systems Corporation, the assignee of the present invention, who sells an EMR database under the trade name of "Chronicles" used with the "EpicCare" electronic medical record software.

The patient communication channel 14 may join the interface module 12 to a web server 22 providing a secure socket layer connection to the Internet 24. The Internet 24 may in turn connect a number of patient terminals 26 (only one shown for clarity) implementing a browser and/or a kiosk 28, provided, for example, at a doctor's office or elsewhere, either or both of which are used by a patient 30.

The web server 22 includes a number of active web pages 32, some of which will be described below, allowing the patient and/or monitoring system 28 to transmit and receive data securely to and from the web server 22. Incorporated into these web pages 32, for example as a CGI script, is a program for authentication of the patient's access to the web pages 32. The authentication control program makes use of a log-in identifier/password validation table 34 both shown as logically held on the web server 22 but in the preferred embodiment stored and executed remotely. The login identifier/password validation table 34 holds one or more patient specific tokens (for example, log-in identifiers and passwords but possibly including instead or in addition biometric data and the like) that ensure access to possibly sensitive medical data is not freely available to unknown parties. The patient 30 may also allow access to his or her medical records by a proxy or patient's representative also stored as links in the log-in password/password validation table 34 which gives each proxy a unique token. Generally, the term "patient" as used herein should be considered to include the patient and/or the patient's proxies. One important proxy, of a parent for children, may be initiated as a reminder based on knowledge about childbirth from the EMR.

The patient 30 must enter the text passwords and PIN password upon every new communication session. The text password and PIN password are not stored in cookie form on the patient terminal 26 or kiosk 28 such as might make anyone with access to the patient terminal 26 or kiosk 28 able to view or enter data on behalf of the patient 30. The table 34 may also include provisions allowing several different text passwords and PIN passwords to be associated with the same patient so that proxy access may be had by a patient's representative.

Data received by the web server 22 from the patient 30 is marked with a patient identification number and forwarded along the patient communication channel 14 as a patient identified message 36 to the interface module 12. Similar messages 36 may be received by the web server 22 along the patient communication channel 14 from the interface module and forwarded to the patient 30. Generally the messages 36 will be formatted to act as queries or responses to queries of or from the EMR database 18.

Referring still to FIG. 1, the interface module 12 may also connect to a provider communication channel 40 possibly using all or a portion of standard EMR network 19 allowing communication with healthcare sources 20 via terminals 42 associated, for example, with a primary care physician 44, a system administrator 46, laboratory services, and other service and resource providers. The resources may have access to the EMR database 18 directly per normal conventions or through the interface module 12 as will be described using a viewer/editor 48.

Access through the interface module 12 by the physician 44 also provides limited access to the patient 30. In this respect, some patient data in messages 36 sent by the patient 30 can be routed to a physician 44 and messages from the physician 44 may be routed to the patient 30 in the form of secure communications. Such email communications may also be initiated by the patient 30 as will be described further below.

Interface module 12 may further include a specialized care module 50 configured to compare a reason received from the patient 30 with data from the EMR 18 to determine if the received reason/EMR data combination indicates that the patient 30 needs specialized care and/or scheduling. For example, a patient desiring to schedule an appointment with her doctor that provides a reason "having elbow pain" will be presented with different, more or less expedited, scheduling options where the patient's EMR indicates that she has a history of tennis elbow compared to a history of hypertension, both of which conditions may be reflected in the data stored in EMR 18.

Alternatively, the type of resources being scheduled may be affected by the provided combination of a selected reason and EMR 18 data. For example, a diabetic patient having foot pain may be scheduled to be seen by a podiatrist that specializes in care of diabetic patients and the complication that may arise based on the diabetes.

A listing of combinations may be generated and stored in tables in a database 62 associated with EMR network 19. The listing of combinations may be generated based on data typically generated by healthcare workers and stored in an EMR. For example, the above selected reason of "having elbow pain" may have different specialized scheduling instructions stored in database 62 for EMR data 18 indicating recent surgery, hypertension, a history of overuse injuries, a bone disorder, etc. Preferably, each reason may also be associated with default scheduling instructions where the EMR 18 data does not indicate that any specialized scheduling is required.

The combinations stored in database 62 may be generated based upon commonly accepted principles of medicine that are well known in the art. Additionally, the combinations stored in database 62 may be configured to be modifiable by healthcare provider institutions, individual practitioners, etc. For example, in one area of the country, a patient providing a specific reason/EMR 18 data combination may be scheduled differently from other areas. A patient in the rural desert southwest whose EMR 18 data indicates a shortly prior visit of muscle aches after returning from a camping trip and now provides a reason of "shortness of breath," may be scheduled for a hantavirus screening.

Figure 2:
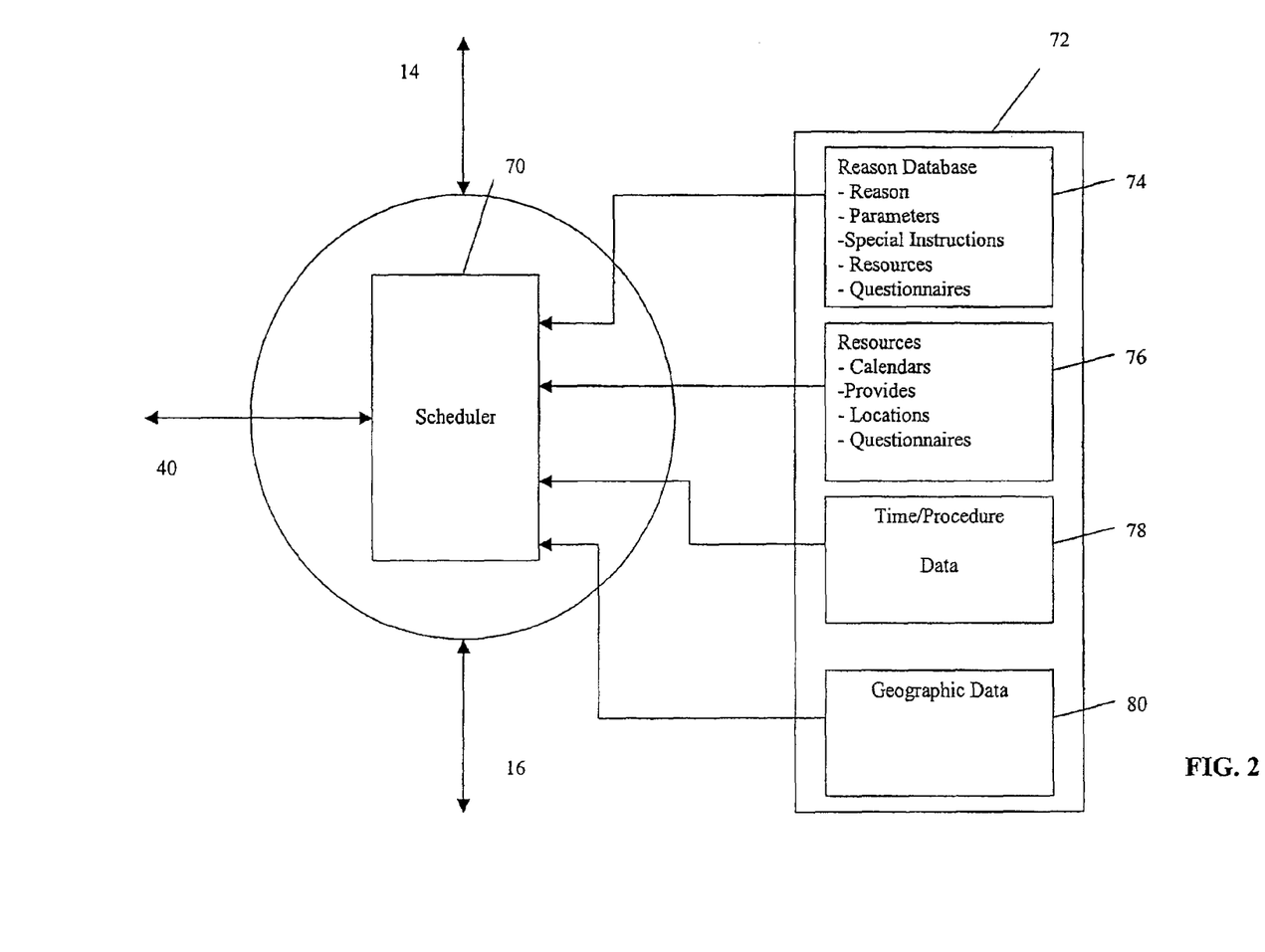
FIG. 2 is a detailed block diagram of the interface of FIG. 1 showing a scheduler and associated scheduling databases.

Referring now to FIGS. 1 and 2, the interface module 12 includes a scheduler 70 which includes a set of rules for scheduling appointments based on scheduling data found in a schedule database 72, data from the EMR 18 and data input at the server 22 by the patient 30 at a patient terminal which can be as described above at terminal 26 or kiosk 28. The scheduling database 72 can include a procedure or reason database 74, one or more resource database 76, time/procedure data 78 for correlating time periods to selected reasons or procedures, and geographic data 80, providing a location of a given resource and data correlating expected time to travel between one resource and others. The procedure or reason database 74 includes a series of possible reasons for an appointment along with parameters for determining whether a patient is eligible for the selected procedure, a list of resources required for the requested procedure and special instructions associated with the requested procedure. Such instructions can include information required by the patient such as, for example, the need for fasting prior to the procedure.

The resource database 76 can include medical resources which can be, for example, individual practitioners, clinics, medical equipment such as X-ray, CT, or MRI machines, laboratory resources or other practitioners' equipment or processes that need to be used in a medical procedure. Group meetings, such as educational meetings scheduled for a group of patients, can also be a resource. Detailed sets of questions (referred to hereafter as questionnaires) for acquiring information required from the patient, can be included with both the reason database 74 and the resource database 76. The questionnaires can be provided to the patient at the patient terminal 30, and the scheduler 70 therefore obtains required data from the patient based on the medical reason for the visit, the specific requirements of the provider or a clinic, and based on the requirements for a specific resource. Furthermore, patient information can be pulled from the EMR database 18 to populate portions of the questionnaire prior to providing the questionnaire to the patient, thereby minimizing the amount of input information required from the patient and increasing the efficiency of the scheduling system. Data from the EMR database 18 can also be used to filter the questions provided to the patient based on known data about the patient.

Although a number of separate databases with specific information are shown and described, it will be apparent that there are a number of ways to arrange and coordinate the data required for the scheduling process, any of which could be used as described herein. Furthermore, although the scheduling database 72 is shown in conjunction with the interface module 12, it will be apparent that the database can be provided at the server 22, as part of the EMR 18, in a separate memory component accessible to parts of the system, or elsewhere.

Figure 3:
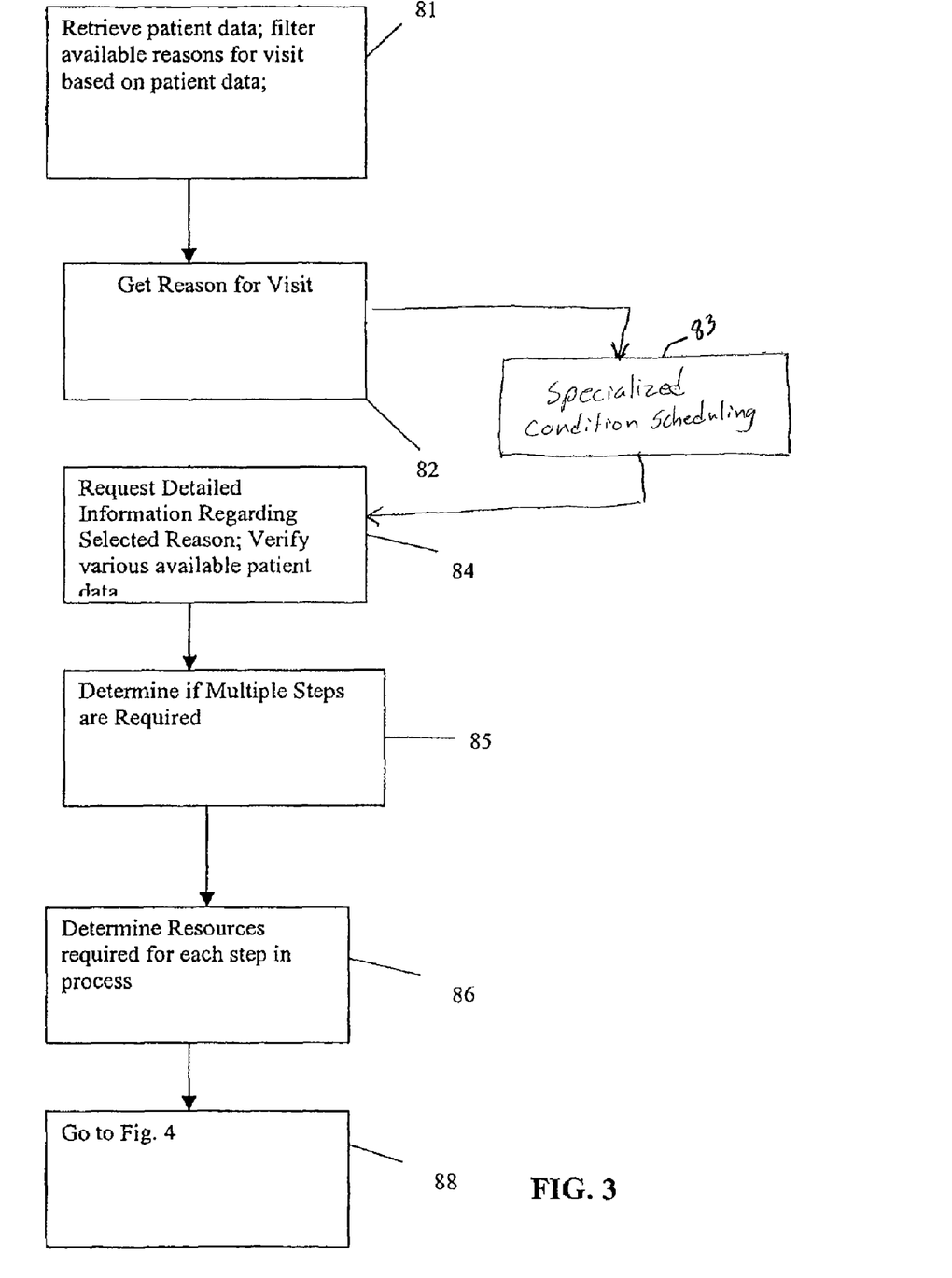
FIG. 3 is a flow chart showing the steps of data flow for retrieving a reason for an appointment from a patient.

Referring now to FIGS. 3-5, the operation of the scheduler 70 (FIG. 2) is shown. Referring first to FIG. 3, based on the patient identification, the scheduler 70 in process block 81 retrieves data from the EMR 18 (FIG. 1) regarding, for example, the age, sex, and medical condition of the patient, and filters the possible reasons for an appointment in reason database 74 based on these patient parameters to eliminate error and/or unnecessary selections. The scheduler 70 then queries the patient for a reason for an appointment, preferably by providing a menu of possible reasons on a page provided to the patient 30 from the web server 22. The user then selects a reason for the visit, as shown in process block 82. Although the process has been described as filtering possible reasons and presenting a menu, it will be apparent that the reason could also be entered as text or voice data. Furthermore, although shown and described as starting the process with entering a reason, the order and type of questioning could be varied such that, for example, the initial query is to select a provider, department, specialty, or facility. Any or all of these selections can be used to start the scheduling process. Although the invention is descried with reference to a particular order, the invention is not intended to be limited to any particular order.

In a step 83, scheduler 70 is configured to allocate resources based on the data from EMR 18 in combination with the received reason selected from reason database 74 to perform a scheduling function for patients having a specialized condition. Scheduler 70 is configured to interpret data from EMR 18 in combination with the received reason to recognize combinations that warrant unique resource scheduling. For example, a patient indicated as being diabetic based on their EMR 18 data who is scheduling an appointment with a podiatrist complaining of sore feet may be presenting with early signs of complication relating to their diabetic condition. The patient may be presented with scheduling options that are unique to the provided combination. For example, a scheduling option to see a particular podiatrist that specializes in the complication that occur when a patient has diabetes may only be presented where a patient 30 has indicated foot pain as his selected reason and his EMR 18 data indicates that he has been previously diagnosed by a healthcare provider as having diabetes. Although the above provided example provides one example of using a combination of EMR 18 data and a patient selected reason to provide customized scheduling options, one of ordinary skill in the art would understand that customized scheduling may include providing access to specialized practitioners, resources, scheduling additional procedures, etc.

After the initial data, such as a reason, has been received, the scheduler 70, in process block 84, requests detailed information associated with the request. The data request can be in the form of a questionnaire which can be, as described above, provided to the patient at the terminal 26 or kiosk 28, or, alternatively, retrieved from stored preferences selected by the patient. This information can include, for example, medical history, patient preferences such as language and gender of the caregiver, time and place of appointment, and other information required or desirable to process the request for an appointment. For example, a patient completing the questionnaire may indicate claustrophobia, in which case, for example, open MRI machine scheduling options may be required. Based on the more detailed information retrieved in block 84, the scheduler 70 determines if multiple steps are required. For example, a procedure can be a visit to a medical practitioner, or consist of a multi-step process including laboratory testing and analysis followed by an appointment with a medical practitioner to review the results. Once the steps are determined, in process block 86, the scheduler 70 determines the resources required and, in process block 88, continues to FIG. 4 for scheduling and resource allocation.

Figure 4:
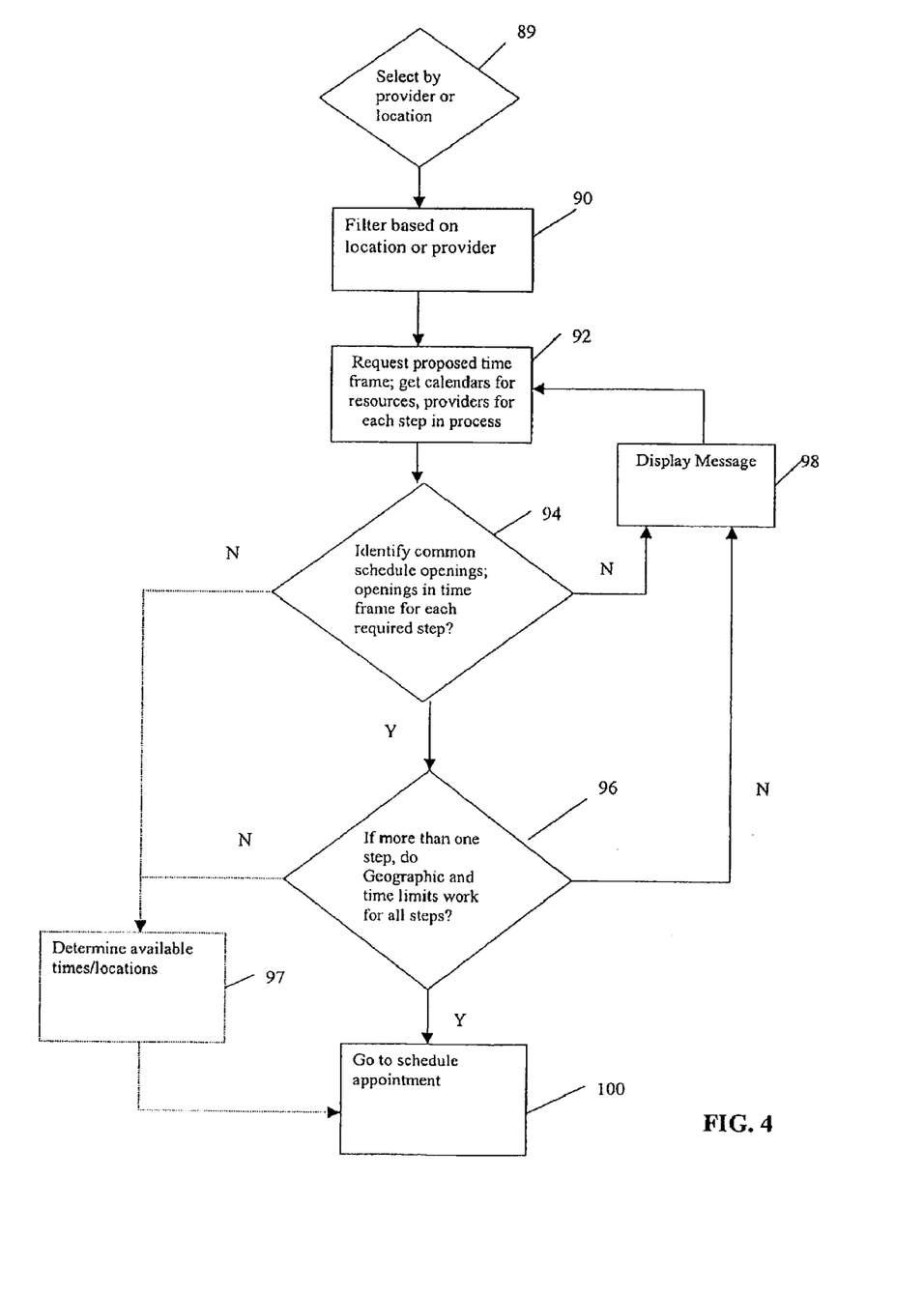
FIG. 4 is a flow chart showing the steps for determining one or more schedule option.

Referring now to FIG. 4, in process block 89, the user is given the option of selecting either a location for the procedure or a medical provider, and in process block 90 resources are filtered by the scheduler 70 based on whether the patient would prefer a specific practitioner or a specific location. In process block 92, the scheduler system 70 also requests a proposed time frame for scheduling the procedure from the patient 30, and then accesses calendars or schedules in resource database 76 for the required resources for each step in the process. In process block 94, the scheduler 70 identifies common schedule openings between the resources required within the time frame specified by the patient. If the resource required cannot be scheduled within the time frame selected, a patient message is displayed in process block 98 and the patient is again queried regarding a proposed time frame, or, alternatively, in process block 97, the scheduler 70 generates a list of alternatives. These alternatives can include, for example, appointments at the same time but with different providers, appointments at the same time but at a different location, appointments with the same provider at a different time on an adjacent date, etc. After this list is generated, the scheduler proceeds to scheduling an appointment in process block 100.

Figure 5:
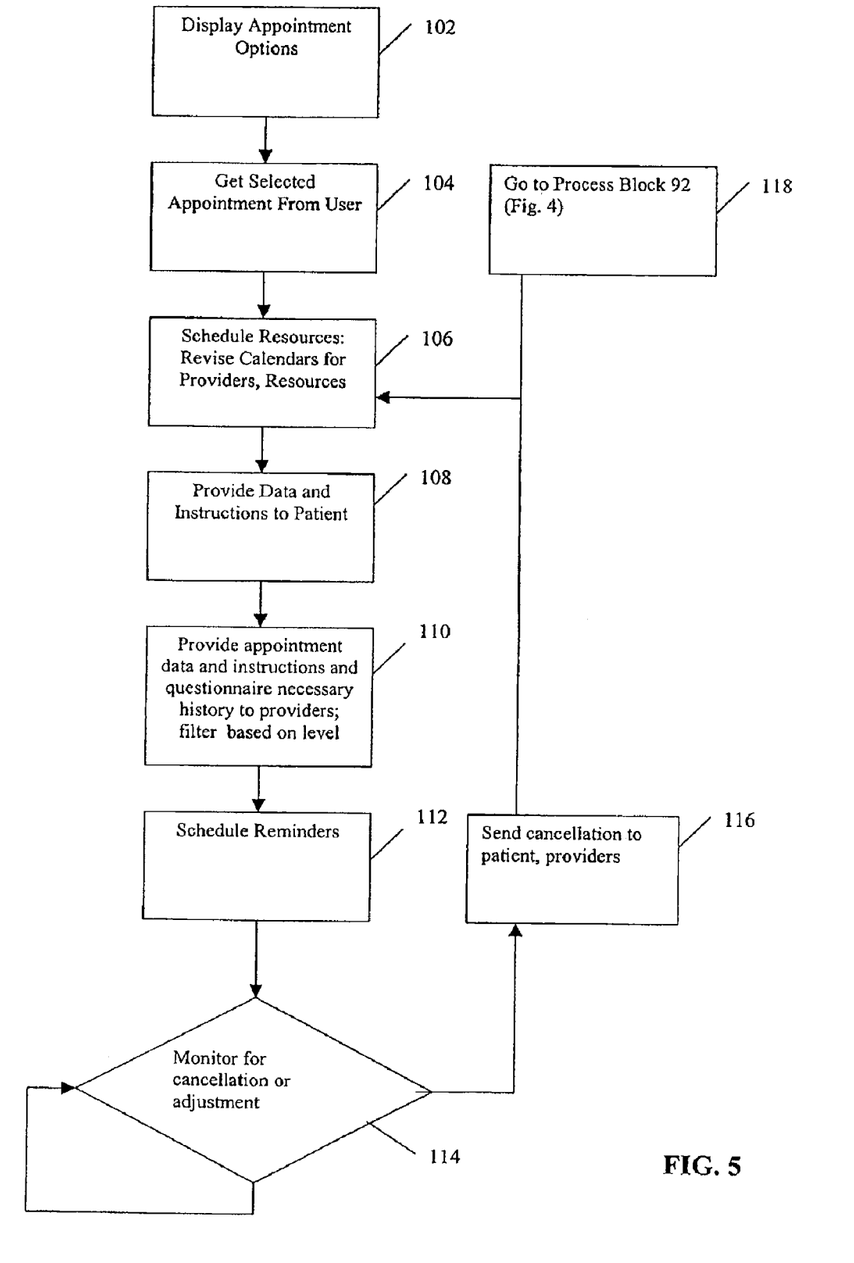
FIG. 5 is a flow chart showing the steps for scheduling an appointment and providing reminders.

If common schedule openings are found, in process block 96, and more than one step is required for the procedure, the time required for each step and the geographic distance between the related resources in the various steps are retrieved from the database 72, and the scheduler 70 determines whether the series of steps are compatible such that a patient could, within the required time frames, and within the cited geographical distances, complete all the steps of the procedure. For example, therefore, if laboratory tests are required before meeting with a medical practitioner, the scheduler 70 retrieves data to determine the amount of time that is required to process the laboratory data and transmit it to the medical practitioner, and how long it will take the patient to travel from the laboratory to the office of the medical practitioner. If the time and geographical requirements can be met, scheduling options are available. Once options are determined by the scheduler 70, the process proceeds to allow a patient to select a scheduling appointment from at least one and preferably a series of possible appointments as shown in FIG. 5. If not, the patient is returned to process block 92 and queried for another time frame.

Referring now to FIG. 5, in process block 102, one or more schedule opening have been determined and options for scheduling an appointment are displayed to the patient. While a number of possible schedule options can be displayed, the patient is prevented from viewing the entire schedule of any given practitioner or other resource. At no time, therefore, is the entire schedule displayed to the patient. In process block 104, the patient selects one of the scheduling options presented, and in process block 106, the scheduler 70 allocates the selected resources by revising the associated calendars in database 76 for each of the providers and/or resources that are required. If the procedure includes multiple steps, the scheduler 70 stores a linkage or log of the separate steps which can be used both for distributing information to the various resources in the log, and also for changing or canceling appointments as described below.

In process block 108, the finalized scheduling data is provided to the patient and the patient is provided with any special instructions required for the procedure. This notification can be provided directly to the kiosk 28 or computer 26, to a secure messaging address provided by the patient, or in the alternative through a voice automated voice-mail system or using various other user-selectable communication methods. The appointment data, instructions provided to the patient, the questionnaire data, and any necessary history required from the EMR 18 are also provided to the service providers and/or resource managers preferably through electronic communications such as secure messaging. The data provided to medical personnel can be filtered depending on the level of the service provider, and/or on a need-to-know basis. Furthermore, any additional patient questionnaires required from either the practitioner, a medical facility, or required for the use of a given resource can also be transmitted to the patient for completion, and the completed questionnaires transmitted to the necessary parties. As described above, patient information can be pulled from the EMR database 18 to populate portions of the questionnaire prior to providing the questionnaire to the patient.

Once both the resources and the patient are notified, the scheduler 70, in process block 112, schedules reminders to be sent to the patient and/or service providers. The reminders can be spaced either at a predetermined preset time or at a time frame selected by the patient and/or service providers. Again, these reminders can be e-mailed, provided through an automated voice-mail system, or provided through other user-specified communication channels such as secure messaging. After the reminders are scheduled, the scheduler 70 continues to monitor for cancellation either by the patient or one of the service provides or resources, or for an appointment change or adjustment provided by the service provider or a resource manager, as shown in process block 114. If a cancellation or adjustment request is received, a cancellation or adjustment notice is forwarded to the patient and to the associated providers in process block 116. In the case of an adjustment, the patient 30 can be given the option to accept the adjustment or start the scheduling process over. If a cancellation occurs or an adjustment is accepted, the calendars in database 76 for the service providers and associated resources are revised to reflect the fact that the time frames for use of the resources has changed. As necessary, a request can be forwarded to the patient 30 to enter a new time frame request. When an adjustment or a cancellation is made to a multi-step procedure, the scheduler 70 retrieves the log or linkage information for the steps, and cancels or adjusts all of the steps in the procedure as required.

The present invention therefore provides a number of important improvements in medical resource scheduling. As the scheduler 70 is connected to a database of patient information, the plausibility of a requested medical service can be verified for a specific patient, thereby limiting scheduling errors which can result in resources being tied up unnecessarily. Furthermore, the present invention simplifies and improves the efficiency of patient scheduling by limiting the number of personnel who need to be involved in the scheduling process, and by automating both the distribution of patient instructions and the collection of patient data required for a selected medical procedure, resource, or facility. Moreover, because the system is tied directly to patient data, detailed information about the patient can be easily and efficiently provided to medical service providers and managers with minimal keying of data by either the patient or the medical provider. Additionally, the scheduler 70 can tailor the length of an appointment to the requested medical procedure, thereby increasing the efficiency of medical practices. For medical procedures having multiple steps, the scheduler 70 can verify both time and geographic constraints, and further, can assure that all resources are notified in the event of a cancellation. The scheduler 70 can further filter the schedule options provided to a patient to prevent the patient from viewing the entire schedule of a service provider.

Although a specific data flow is described above, it will be apparent that variations in the order of data flow and retrieval can be made without departing from the invention. Furthermore, although specific hardware configurations are described schematically, it will be apparent that the invention can be used in conjunction with any number of different hardware and architecture configurations.

It is specifically, therefore, intended that the present invention not be limited to the embodiments and illustrations contained herein, but include modified forms of those embodiments including portions of the embodiments and combinations of elements of different embodiments as come within the scope of the following claims.

We claim:

1. A computer-implemented scheduling system for scheduling patient appointments, comprising:
   a) a patient interface terminal configured to receive a patient identifier and to display a patient-specific listing of reasons for a medical appointment; and
   b) a computer system adapted for
      receiving the patient identifier;
      generating the patient-specific listing of reasons for a medical appointment based on a comprehensive listing of reasons stored in a reasons database, wherein each reason for a medical appointment is associated with a default set of medical resources necessary for the medical appointment;
      receiving a selection of a reason for a medical appointment;
      retrieving data from an electronic medical record associated with the patient identifier;
      determining that the default set of medical resources is not advised based on the data from the electronic medical record in combination with the selected reason for a medical appointment by referencing a database of specialized combinations wherein each reason is associated with one or more medical condition typically indicated in the electronic medical record, each combination of reason and medical condition being associated with specialized appointment scheduling options, the specialized appointment scheduling options including scheduling options for specialized medical resources specifically associated with the combination;
      identifying one or more specialized medical resources based on the determination;
      generating and providing one or more specialized appointment scheduling options for the specialized medical resources specifically associated with the combination, the specialized medical resources being different from the default set of medical resources;
      providing instructions for a patient at the patient interface terminal to prepare for the medical appointment based on the selected reason; and
      providing a questionnaire at the patient interface terminal to obtain data from the patient prior to the medical appointment based on the selected reason.

2. The scheduling system of claim 1, wherein the medical resources include at least one of a geographic location, a healthcare provider, and medical equipment.

3. The scheduling system of claim 1, wherein the specialized medical resources are different than the medical resources.

4. The scheduling system of claim 1, wherein the medical resource is a geographic location and the scheduling option is for a plurality of appointments, and wherein the scheduling options are generated based on a travel time between geographic locations associated with the plurality of appointments.

5. The scheduling system of claim 1, wherein the patient interface terminal is further configured to present schedule options based on receiving a selected reason for a requested medical appointment, wherein the schedule options presented at the patient terminal indicate schedule options for resources available within the range of times.

6. The scheduling system of claim 5, wherein the patient interface terminal is further configured to receive a range of geographic locations acceptable for the appointment and wherein the schedule options presented indicate schedule options for resources available within the range of geographic locations.

7. The scheduling system of claim 5, wherein the computer system communicates with a database providing data indicating appointment lengths linked to types of healthcare service appointments and wherein the presenting of schedule options indicates schedule options accommodating an appointment of the appointment length linked to the type of healthcare service appointment.

8. The scheduling system of claim 5, wherein the schedule options presented indicate only healthcare providers and resources that can coordinate to provide the healthcare service.

9. The scheduling system of claim 1, wherein the computer system further accepts an input from the patient interface terminal for an appointment selected from the schedule options and submits appointment data to a schedule for the healthcare provider.

10. The scheduling system of claim 1, wherein the computer system further accepts an input from the patient interface terminal for an appointment selected from the schedule options and wherein the computer system provides a reminder notification to the patient interface terminal.

11. The scheduling system of claim 10, wherein the computer system further provides the reminder to the patient based on stored patient preferences.

12. The scheduling system of claim 1, wherein the computer system further receives from the patient interface terminal a notice of appointment cancellation and submits cancellation data to a schedule for the resource.

13. The scheduling system of claim 1, wherein the computer system further receives from the patient interface terminal a notice of appointment cancellation and submits cancellation data to a schedule for the healthcare provider to remove the appointment from the schedule.

14. The scheduling system of claim 1, wherein the computer system further receives from the patient interface terminal a notice of appointment and submits appointment data to a schedule for the healthcare provider, the appointment data indicating schedule resources; and wherein the computer system further receives information from the healthcare provider modifying the schedule resources.

15. The scheduling system of claim 1, wherein the computer system includes a central database holding schedules for healthcare providers and resources and accesses the central database to identify healthcare providers for the service and to identify resources required for the service to present schedule options according to common schedule openings of healthcare providers and resources.

16. The scheduling system of claim 15, wherein the common schedule openings are of healthcare providers and resources within a predetermined geographic range.

17. The scheduling system of claim 1, wherein the healthcare service requires multiple sequential steps and wherein the computer system identifies healthcare providers and resources for each step of the service.

18. The scheduling system of claim 17, wherein the computer system presents schedule options at the interface terminal based on the multiple identified providers and resources providing different combinations of the multiple providers and resources.

19. The scheduling system of claim 18, wherein the computer system presents a schedule option for the first available appointment.

20. The scheduling system of claim 19, wherein a first step in the multiple sequential steps requires a test and wherein the computer system communicates with a database providing data indicating laboratory test processing delay associated with the test and wherein the presenting of schedule options indicates schedule options accommodating a test processing delay.

21. The scheduling system of claim 19, wherein the steps require resources and/or healthcare providers at different geographic locations and wherein the computer system communicates with a database providing data indicating travel time delay between the geographic locations and wherein the presenting of schedule options indicates schedule options accommodating travel time delay.

22. The scheduling system of claim 1, wherein the selected medical appointment comprises a plurality of steps, each step including a medical resource, and wherein the computer system is adapted to store a log of an order of the steps.

23. The scheduling system of claim 22, wherein the computer systems is adapted to retrieve the log of the order of steps and to cancel each of the steps in the log when a request for a cancellation is received by the computer system.

* * * * *